(12) United States Patent
Yang et al.

(10) Patent No.: US 8,530,497 B2
(45) Date of Patent: Sep. 10, 2013

(54) CRYSTALLINE SALTS OF A POTENT HCV INHIBITOR

(75) Inventors: Bing-Shiou Yang, Southbury, CT (US); Ka Yip, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 131 days.

(21) Appl. No.: 13/044,027

(22) Filed: Mar. 9, 2011

(65) Prior Publication Data

US 2012/0059033 A1 Mar. 8, 2012

Related U.S. Application Data

(60) Provisional application No. 61/312,791, filed on Mar. 11, 2010.

(51) Int. Cl.
*A61K 31/47* (2006.01)

(52) U.S. Cl.
USPC .......................................... 514/312

(58) Field of Classification Search
None
See application file for complete search history.

(56) References Cited

U.S. PATENT DOCUMENTS

| | | |
|---|---|---|
| 6,323,180 B1 | 11/2001 | Llinas-Brunet et al. |
| RE40,525 E | 9/2008 | Llinas-Brunet et al. |
| 7,514,557 B2 | 4/2009 | Busacca et al. |
| 7,585,845 B2 | 9/2009 | Llinas-Brunet et al. |
| 8,232,293 B2 | 7/2012 | Berkenbusch et al. |
| 2005/0020503 A1 | 1/2005 | Llinas-Brunet et al. |
| 2010/0093792 A1 | 4/2010 | Berkenbusch et al. |

FOREIGN PATENT DOCUMENTS

| | | |
|---|---|---|
| WO | 0009543 A2 | 2/2000 |
| WO | 2004087741 A1 | 10/2004 |
| WO | 2004103996 A1 | 12/2004 |
| WO | WO 2004/103996 * | 12/2004 |
| WO | 2010033444 A1 | 3/2010 |
| WO | 2011112761 A1 | 9/2011 |

OTHER PUBLICATIONS

S.M. Berge et al., J. Pharm. Sci., 1977, 66 pp. 1-19.*
International Search report, Form PCT/ISA/220, and Written Opinion, Form PCT/ISA/210, for application PCT/US2011/027807, date of mailing May 10, 2011.
Caira et al., Crystalline Polymorphism of Organic Compounds, Topics in Current Chemistry, 1998, vol. 198, pp. 163-208, ISSN: 0340-1022.

* cited by examiner

*Primary Examiner* — Craig Ricci
(74) *Attorney, Agent, or Firm* — Michael P. Morris; Philip I. Datlow

(57) ABSTRACT

This invention relates to novel tris(hydroxymethyl)aminomethane, choline and N-methyl-D-glucamine salt forms of the following Compound (1) and methods for the preparation thereof, pharmaceutical compositions thereof, and their use in the treatment of Hepatitis C Viral (HCV) infection:

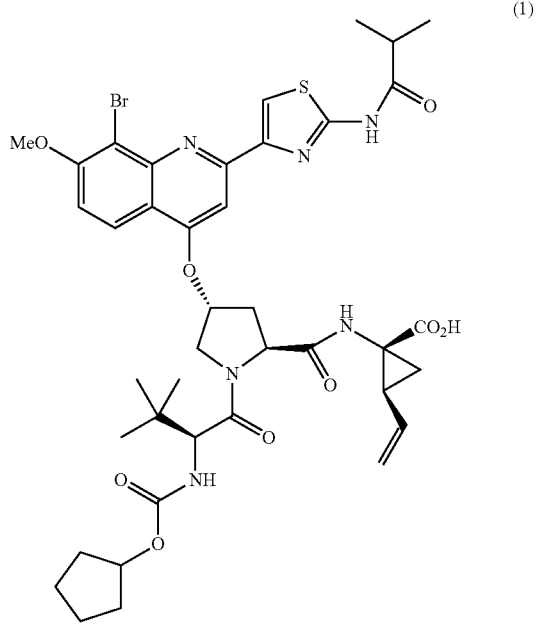

(1)

10 Claims, 6 Drawing Sheets

CRYSTALLINE SALTS OF A POTENT HCV INHIBITOR

FIELD OF THE INVENTION

This invention relates to novel crystalline salts of Compound (1) as described herein, methods for the preparation thereof, pharmaceutical compositions thereof, and their use in the treatment of Hepatitis C Viral (HCV) infection.

BACKGROUND OF THE INVENTION

The following Compound (1):

(1)

is known as a selective and potent inhibitor of the HCV NS3 serine protease. Compound (1) falls within the scope of the acyclic peptide series of HCV inhibitors disclosed in U.S. Pat. Nos. 6,323,180, 7,514,557 and 7,585,845. Compound (1) is disclosed specifically as Compound #1055 in U.S. Pat. No. 7,585,845, and as Compound #1008 in U.S. Pat. No. 7,514,557. Compound (1) can be prepared according to the general procedures found in the above-cited references, which are herein incorporated by reference.

Compound (1) may also be known by the following alternate depiction of its chemical structure, which is equivalent to the above-described structure:

wherein B is $L^0$ is MeO—; $L^1$ is Br; and $R^2$ is

When synthesized according to the general procedures set forth in the above-cited references, Compound (1) is prepared as an amorphous solid which is a form that is to generally less suitable for full-scale pharmaceutical processing. Thus, there is a need to produce Compound (1) in a crystalline form to enable formulations to meet exacting pharmaceutical requirements and specifications. Furthermore, the process by which Compound (1) is produced needs to be one which is amenable to large-scale production. Additionally, it is desirable that the product should be in a form that is readily filterable and easily dried. Finally, it is economically desirable that the product be stable for extended periods of time without the need for specialized storage conditions.

U.S. patent application Ser. No. 12/559,927, filed Sep. 15, 2009, discloses the Type A crystalline form of Compound (I) and a crystalline sodium salt form of Compound (I) with more favorable pharmaceutical properties compared to the amorphous compound. However, the crystalline sodium salt is a variable hydrate which may impose challenges in production, e.g. challenges in consistent formulation characterization, manufacturing (e.g. difficulty drying) and handling. Salts with superior properties compared to the Type A crystalline form of Compound (I) and the crystalline sodium salt, e.g. a non-solvated crystalline form, would be preferred for large scale production and pharmaceutical formulation.

SUMMARY OF THE INVENTION

We have now surprisingly and unexpectedly found for the first time that Compound (1) can be prepared in the crystalline tris(hydroxymethyl)aminomethane (tromethamine) form and also in the form of its crystalline choline salt, and its crystalline N-methyl-D-glucamine salt. Thus, the present invention provides Compound (1) in new crystalline salt forms, which in one embodiment is the new crystalline tromethamine salt and additional embodiments include the crystalline choline salt and the crystalline N-methyl-D-glucamine salt. These novel crystalline forms overcome the pharmaceutical processing difficulties inherent in the use of an amorphous form and, also, in particular, the tromethamine and choline salts have other properties making them particularly advantageous compared to the crystalline Type A and sodium salt forms in pharmaceutical formulation processing as will be described in detail below.

These novel crystalline forms of Compound (1) may be characterized and distinguished from one another using various techniques, including X-Ray Powder Diffractometry (XRPD) and Solid State NMR (ssNMR).

In one embodiment, the present invention is directed to Compound (1) in crystalline tromethamine salt form referred to herein as "TH".

Another embodiment is directed to the crystalline choline salt of Compound (1), referred to herein as "HEA".

Another embodiment is directed to the crystalline N-methyl-D-glucamine salt of Compound (1), referred to herein as "MU".

Additional embodiments include each of the TH, HEA and MU salts as characterized by either XRPD or ssNMR or both XRPD and ssNMR.

Yet another embodiment is directed to a pharmaceutical composition comprising TH, HEA or MU or mixtures thereof, and at least one pharmaceutically acceptable carrier or diluent.

Yet another embodiment is directed to a method of treating HCV infection in a mammal comprising administering to said mammal a therapeutically effective amount of TH, HEA or MU, or mixtures thereof.

DETAILED DESCRIPTION OF THE INVENTION

Definitions

Terms not specifically defined herein should be given the meanings that would be given to them by one of skill in the art in light of the disclosure and the context. As used throughout the present application, however, unless specified to the contrary, the following terms have the meaning indicated:

The term "TH" means the crystalline tromethamine salt of Compound (1).

The term "HEA" means the crystalline choline salt of Compound (1).

The term "MU" means the crystalline N-methyl-D-glucamine salt of Compound (1).

The term "about" means within 5%, and more preferably within 1% of a given value or range. For example, "about 3.7%" means from 3.5 to 3.9%, preferably from 3.66 to 3.74%. When the term "about" is associated with a range of values, e.g., "about X % to Y %", the term "about" is intended to modify both the lower (X) and upper (Y) values of the recited range. For example, "about 20% to 40%" is equivalent to "about 20% to about 40%".

The term "pharmaceutically acceptable" with respect to a substance as used herein means that substance which is, within the scope of sound medical judgment, suitable for use in contact with the tissues of humans and lower animals without undue toxicity, irritation, allergic response, and the like, commensurate with a reasonable benefit/risk ratio, and effective for the intended use when the substance is used in a pharmaceutical composition.

The term "treating" with respect to the treatment of a disease-state in a patient include
(i) inhibiting or ameliorating the disease-state in a patient, e.g., arresting or slowing its development; or
(ii) relieving the disease-state in a patient, i.e., causing regression or cure of the disease-state. In the case of HCV, treatment includes reducing the level of HCV viral load in a patient.

Crystalline TH

The Compound (1) has been isolated as a crystalline tromethamine salt polymorph designated herein as "TH" and has been characterized using X-Ray Powder Diffractometry (XRPD), Differential Scanning calorimetry (DSC), and Solid State NMR (ssNMR).

In general, TH exhibits a characteristic X-ray powder diffraction ("XRPD") pattern with the higher intensity peaks expressed in degrees 2θ (±0.2 degrees 2θ) at 5.9, 9.8, 10.0, 16.4, 16.7, 20.3, 20.9, and 22.6

Figure 1:
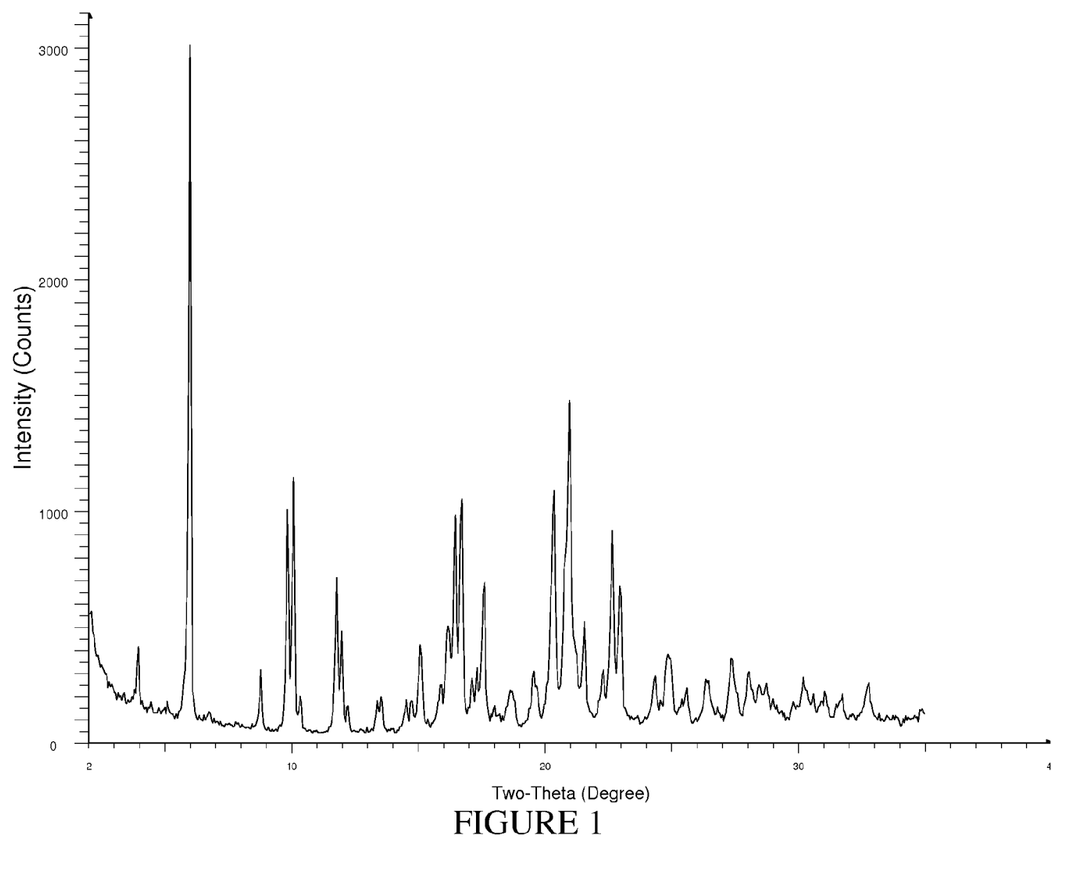
FIG. 1 is a characteristic X-ray Powder Diffraction pattern for crystalline TH.

The XRPD pattern of TH is shown in FIG. 1. The characteristic peak positions and relative intensities for the XRPD pattern in FIG. 1 is shown in Table 1 below (including both higher and lower intensity peaks).

TABLE 1

| Angle, 2θ, ° | Relative Intensity % |
|---|---|
| 3.9 | 14.1 |
| 5.9 | 100.0 |
| 8.8 | 10.6 |
| 9.8 | 33.5 |
| 10.0 | 38.1 |
| 11.7 | 24.0 |
| 12.0 | 16.3 |
| 15.1 | 14.4 |
| 16.1 | 17.0 |
| 16.4 | 33.0 |
| 16.7 | 35.3 |
| 17.6 | 23.2 |
| 20.3 | 36.2 |
| 20.9 | 49.4 |
| 21.6 | 17.5 |
| 22.6 | 30.8 |
| 23.0 | 22.9 |
| 24.8 | 13.0 |
| 27.4 | 12.5 |

For TH crystals, Differential Scanning calorimetry (DSC) shows an endothermic melting/decomposition with onset temperature at 201° C. Thermogravimetric Analysis (TGA) shows a weight loss of 0.15% up to 165° C. These data indicate TH is a non-solvated crystalline solid form. TH crystals exhibited about <4% moisture gain through 85% RH at 25° C. by Dynamic Vapor Sorption (DVS) indicating non-hygroscopic or slightly hygroscopic properties at conditions used in the analysis.

In one general embodiment, the present invention is directed to the crystalline to tromethamine salt of Compound (1), designated herein as "TH".

Another more specific embodiment is directed to crystalline TH that has at least the following characteristic: an X-ray powder diffraction pattern comprising a peak at 5.9 degrees 2θ (±0.2 degrees 2θ) when measured using CuKα radiation.

Another embodiment is directed to crystalline TH having an XRPD pattern comprising a peak at 5.9 degrees 2θ (±0.2 degrees 2θ) as described above and further comprising peaks at 10.0 and 20.9 and degrees 2θ (±0.2 degrees 2θ) when measured using CuKα radiation.

Another embodiment is directed to crystalline TH having an XRPD pattern comprising a peak at 5.9 degrees 2θ (±0.2 degrees 2θ) as described above and further comprising peaks at 10.0, 16.7, 20.3 and 20.9 degrees 2θ (±0.2 degrees 2θ) when measured using CuKα radiation.

Another embodiment is directed to crystalline TH having an XRPD pattern comprising a peak at 5.9 degrees 2θ (±0.2 degrees 2θ) as described above and further comprising peaks at 9.8, 10.0, 16.4, 16.7, 20.3, 20.9 and 22.6 degrees 2θ (±0.2 degrees 2θ) when measured using CuKα radiation.

Another embodiment is directed to crystalline TH exhibiting an XRPD pattern substantially the same as that shown in FIG. 1.

TH exhibits a Solid-state NMR (ssNMR) pattern having C chemical shifts (including both higher and lower intensity peaks) as reported in Table 2 below.

TABLE 2

| Chemical Shift (ppm) |
| --- |
| 178.3 |
| 176.0 |
| 173.9 |
| 173.1 |
| 160.2 |
| 158.9 |
| 158.0 |
| 156.4 |
| 155.4 |
| 150.2 |
| 147.9 |
| 138.1 |
| 122.6 |
| 116.8 |
| 115.9 |
| 113.5 |
| 112.9 |
| 110.0 |
| 98.6 |
| 78.4 |
| 75.5 |
| 62.1 |
| 59.6 |
| 59.0 |
| 54.2 |
| 53.6 |
| 42.4 |
| 37.5 |
| 36.7 |
| 34.6 |
| 33.9 |
| 33.1 |
| 27.1 |
| 24.2 |
| 22.8 |
| 21.7 |
| 18.6 |

All chemical shifts reported and claimed herein are accurate to within ±0.2 ppm unless otherwise indicated.

Figure 2:
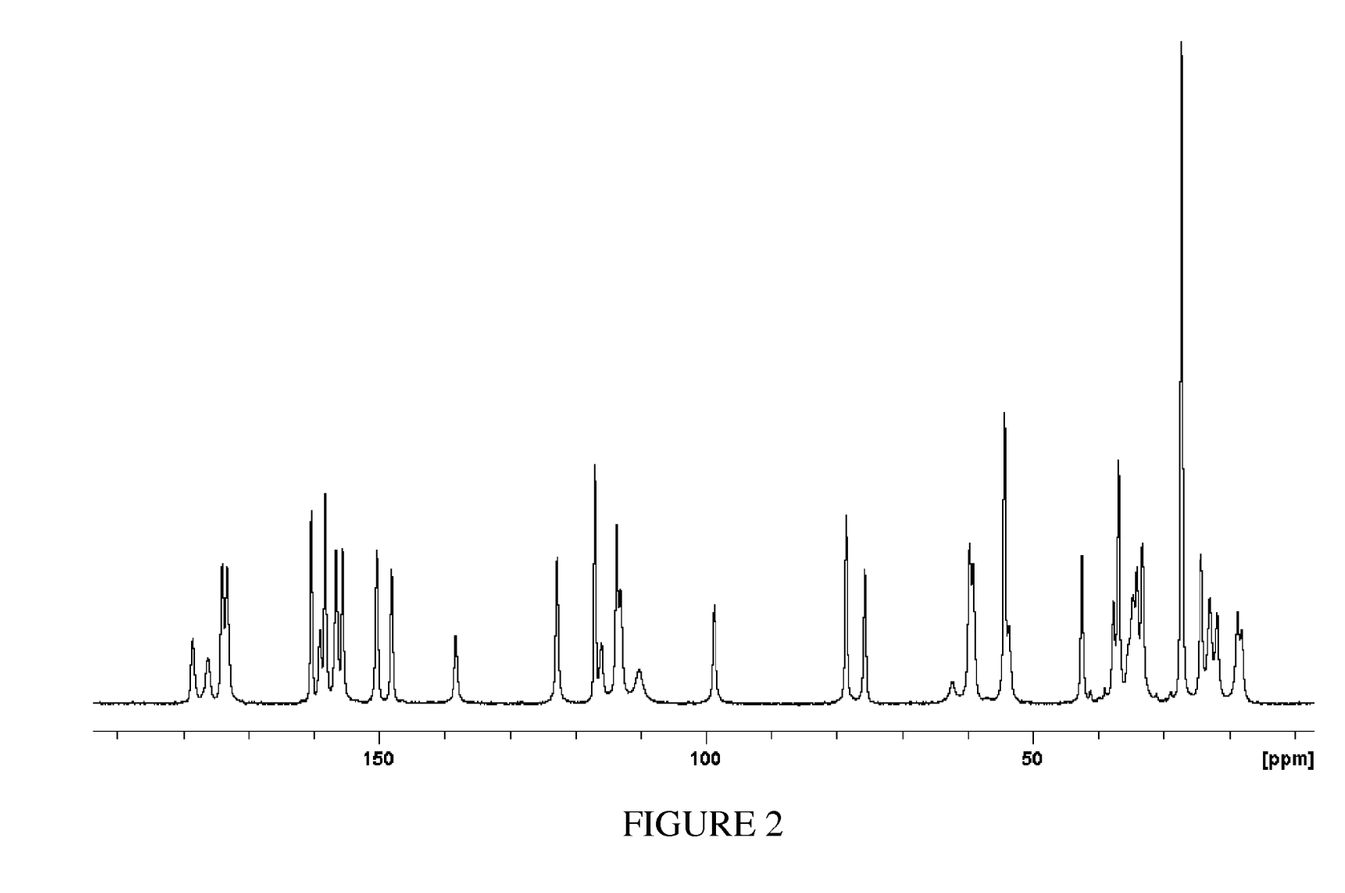
FIG. 2 is a characteristic $^{13}$C Solid State NMR spectrum for crystalline TH.

A representative $^{13}$C ssNMR spectrum of TH is shown in FIG. 2.

One general embodiment is directed to a crystalline tromethamine salt of Compound (1) that has a $^{13}$C solid state NMR spectrum comprising peaks at chemical shifts of 178.3, 138.1 and 27.1 ppm (±0.2 ppm). These chemical shift peaks are believed sufficient to to characterize the TH salt of Compound (1) and distinguish it from other crystalline forms.

Another embodiment is directed to a crystalline tromethamine salt of Compound (1) that has a $^{13}$C solid state NMR spectrum comprising peaks at chemical shifts of 178.3, 173.9, 173.1, 150.2, 147.9, 138.1 and 27.1 (all ±0.2 ppm).

Another embodiment is directed to a crystalline tromethamine salt of Compound (1) that has a $^{13}$C solid state NMR spectrum comprising peaks at chemical shifts of 178.3, 176.0, 173.9, 173.1, 150.2, 147.9, 138.1, 36.7, 27.1, 22.8 and 18.6 ppm (all ±0.2 ppm).

Another embodiment is directed to a crystalline tromethamine salt of Compound (1) exhibiting an $^{13}$C ssNMR spectrum substantially the same as that shown in FIG. 2.

Another embodiment is directed to a crystalline tromethamine salt of Compound (1) having both an XRPD pattern and $^{13}$C ssNMR spectrum according to any combination of the above-mentioned XRPD and $^{13}$C ssNMR embodiments. For example, a crystalline tromethamine salt that has an X-ray powder diffraction pattern comprising a peak at 5.9 degrees 2θ (±0.2 degrees 2θ) when measured using CuKα radiation and a $^{13}$C solid state NMR spectrum comprising peaks at chemical shifts of 178.3, 138.1 and 27.1 ppm (±0.2 ppm).

The present invention provides a process for the preparation of TH which comprises crystallizing TH under conditions described below. The precise conditions under which TH is formed may be empirically determined and it is only possible to give methods which have been found to be suitable in practice.

It has been found that TH may be prepared by a process comprising the following steps, which process is also an embodiment of the present invention:

(i) Combining Compound (1) with 1 equivalent of tris (hydroxymethyl) aminomethane in a suitable solvent;
(ii) Heating the mixture to about 50° C. and stirring for about 3-5 hours;
(iii) Cooling the slurry to about 20° C.;
(iv) Filtering the slurry and rinsing the resulting solid with a suitable solvent;
(v) Drying the solid at about 70° C. under vacuum.

Suitable solvents include acetone and acetonitrile. The preferred solvent is acetone. The resulting crystals of TH may be recovered by any conventional methods known in the art.

In the final steps (iv) and (v), the resulting solids obtained in step (iii) may be collected and dried at high temperature using conventional collection and high-temperature drying techniques, for example, filtration and vacuum oven.

In one preferred embodiment, Compound (1) and 1 equivalent of tris(hydroxymethyl) aminomethane are combined in acetone at a ratio of 10 mL acetone per gram of Compound (1) in step (i), are heated to about 50° C. and stirred for 4 hours in step (ii) and rinsed with acetone in step (iv).

In another embodiment, in step (iii) the slurry is stirred while cooled for about 4-12 hours.

In another embodiment, seeds of TH, obtained from a previous preparation are added during step (ii).

In another embodiment, the solid is dried for about 4 to 12 hours in step (v).

The process steps may of course be facilitated by conventional agitation techniques, e.g., stirring, and other conventional techniques as would be well understood for facilitating the process.

Crystalline HEA

The Compound (1) has been isolated as a crystalline choline salt polymorph designated herein as "HEA". In general, HEA exhibits a characteristic X-ray powder diffraction ("XRPD") pattern with higher intensity peaks expressed in degrees 2θ (±0.2 degrees 2θ) at 7.5, 14.2, 14.9, 17.5, 21.8, 22.1, 22.7 and 24.3.

Figure 3:
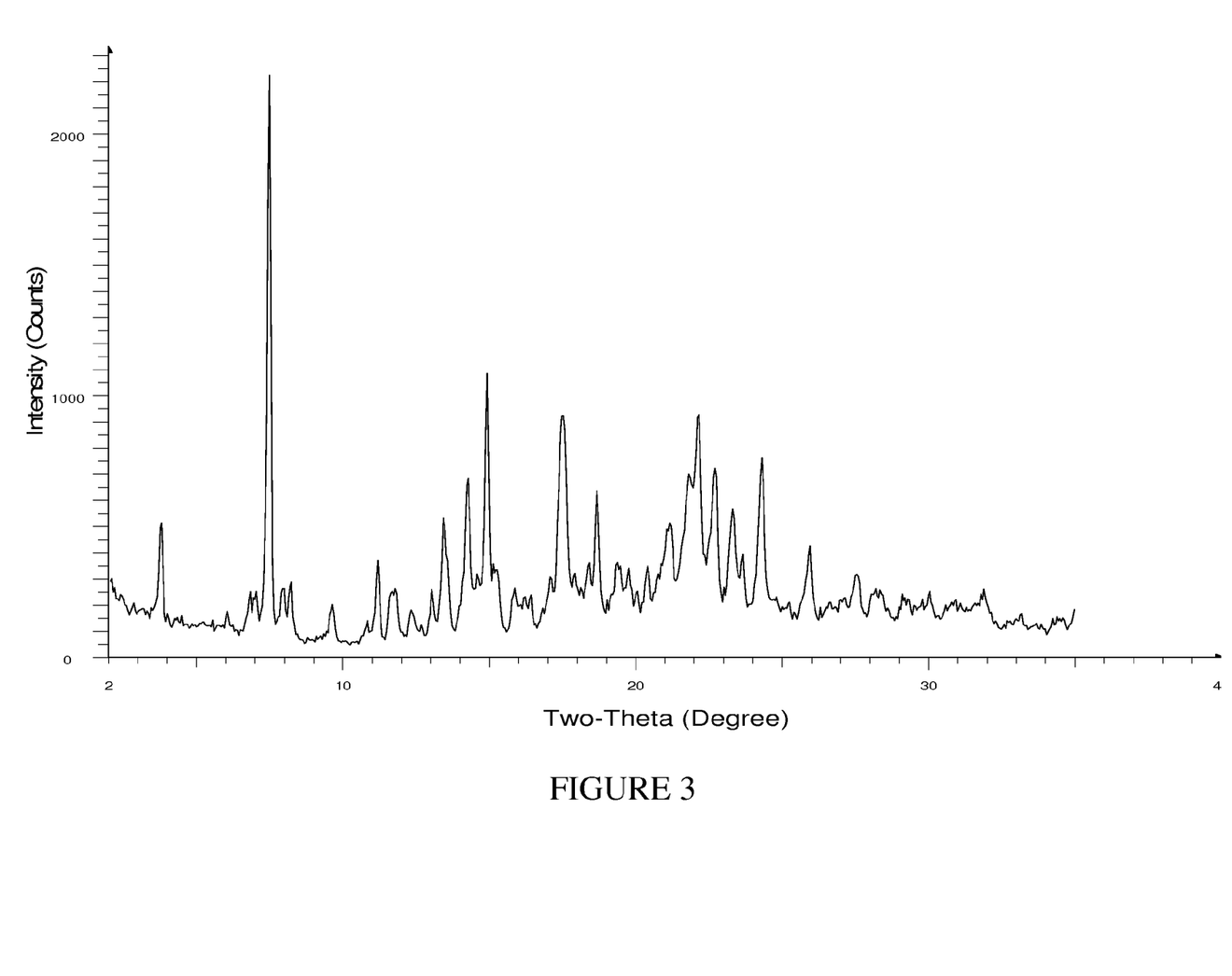
FIG. 3 is a characteristic X-ray Powder Diffraction pattern for crystalline HEA.

The XRPD pattern of HEA is shown in FIG. 3. The characteristic peak positions and relative intensities for the XRPD pattern in FIG. 3 is shown in Table 3 below (including both higher and lower intensity peaks).

TABLE 3

| Angle, 2θ, ° | Relative Intensity % |
|---|---|
| 3.7 | 23.2 |
| 7.5 | 100.0 |
| 11.1 | 17.1 |
| 13.4 | 24.4 |
| 14.2 | 30.9 |
| 14.9 | 49.0 |
| 17.5 | 41.7 |
| 18.7 | 28.5 |
| 21.2 | 23.2 |
| 21.8 | 31.6 |
| 22.1 | 41.7 |
| 22.7 | 32.7 |
| 23.3 | 25.8 |
| 24.3 | 34.5 |
| 26.0 | 19.2 |

For HEA crystals, Differential Scanning calorimetry (DSC) shows an endothermic melting/decomposition with onset temperature at 264° C. Thermogravimetric Analysis (TGA) shows a weight loss of 0.045% up to 230° C. These data indicate HEA is a non-solvated crystalline solid form. HEA crystals exhibited about <2.5% moisture gain through 85% RH at 25° C. by Dynamic Vapor Sorption (DVS) indicating non-hygroscopic properties at conditions used in the analysis.

In one general embodiment, the present invention is directed to the crystalline choline salt of Compound (1), designated herein as HEA.

Another more specific embodiment is directed to crystalline HEA that has at least the following characteristic: an X-ray powder diffraction pattern comprising a peak at 7.5 degrees 2θ (±0.2 degrees 2θ) when measured using CuKα radiation.

Another embodiment is directed to crystalline HEA having an XRPD pattern comprising a peak at 7.5 degrees 2θ (±0.2 degrees 2θ) as described above and further comprising peaks at 14.9 and 17.5 degrees 2θ (±0.2 degrees 2θ) when measured using CuKα radiation.

Another embodiment is directed to crystalline HEA having an XRPD pattern comprising a peak at 7.5 degrees 2θ (±0.2 degrees 2θ) as described above and further comprising peaks at 14.9, 17.5, 22.1 and 24.3 degrees 2θ (±0.2 degrees 2θ) when measured using CuKα radiation.

Another embodiment is directed to crystalline HEA having an XRPD pattern comprising a peak at 7.5 degrees 2θ (±0.2 degrees 2θ) as described above and further comprising peaks at 14.2, 14.9, 17.5, 21.8, 22.1, 22.7 and 24.3 degrees 2θ (±0.2 degrees 2θ) when measured using CuKα radiation.

Another embodiment is directed crystalline HEA exhibiting an XRPD pattern substantially the same as that shown in FIG. 3.

HEA exhibits a Solid-state NMR (ssNMR) pattern having $^{13}$C chemical shifts (including both higher and lower intensity peaks) as reported in Table 4 below.

TABLE 4

| Chemical Shift (ppm) |
|---|
| 175.1 |
| 172.6 |
| 172.2 |
| 170.2 |
| 169.8 |
| 159.8 |
| 158.6 |
| 157.4 |
| 154.9 |
| 150.3 |
| 149.5 |
| 147.8 |
| 147.1 |
| 137.6 |
| 123.1 |
| 122.3 |
| 116.7 |
| 116.3 |
| 114.9 |
| 113.4 |
| 111.2 |
| 98.3 |
| 80.0 |
| 78.8 |
| 75.5 |
| 68.2 |
| 61.7 |
| 57.2 |
| 56.2 |
| 54.6 |
| 47.9 |
| 35.7 |
| 35.1 |
| 34.5 |
| 33.8 |
| 32.9 |
| 31.0 |
| 27.2 |
| 23.6 |
| 21.7 |
| 19.2 |
| 15.7 |

All chemical shifts reported and claimed herein are accurate to within ±0.2 ppm unless otherwise indicated.

Figure 4:
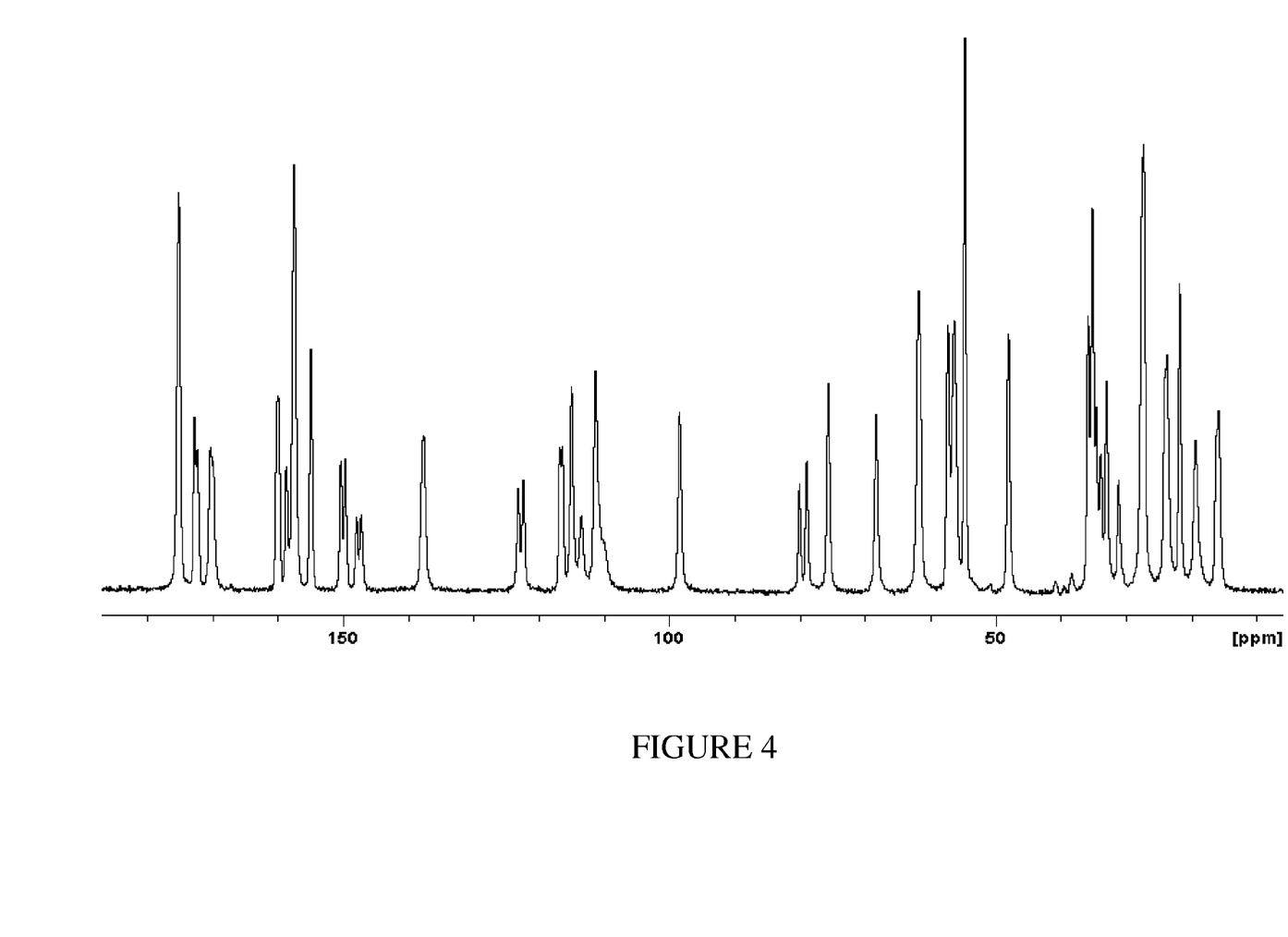
FIG. 4 is a characteristic $^{13}$C Solid State NMR spectrum for crystalline HEA.

A representative $^{13}$C ssNMR spectrum of crystalline HEA is shown in FIG. 4

One general embodiment is directed to a crystalline choline salt of Compound (1) that has a $^{13}$C solid state NMR spectrum comprising peaks at chemical shifts of 175.1, 137.6 and 27.2 ppm (±0.2 ppm). These chemical shift peaks are believed sufficient to characterize the HEA salt of Compound (1) and distinguish it from other crystalline forms.

Another embodiment is directed to a crystalline choline salt of Compound (1) that has a $^{13}$C solid state NMR spectrum comprising peaks at chemical shifts of 175.1, 172.6, 172.2, 147.8, 147.1, 137.6 and 27.2 (all ±0.2 ppm).

Another embodiment is directed to a crystalline choline salt of Compound (1) that has a $^{13}$C solid state NMR spectrum comprising peaks at chemical shifts of 175.1, 172.6, 172.2, 170.2, 154.9, 149.5, 147.8, 147.1, 137.6, 27.2 and 15.7 ppm (all ±0.2 ppm).

Another embodiment is directed to the crystalline choline salt of Compound (1) exhibiting an $^{13}$C ssNMR spectrum substantially the same as that shown in FIG. 4.

Another embodiment is directed to a crystalline choline salt of Compound (1) having both an XRPD pattern and $^{13}$C ssNMR spectrum according to any combination of the above-mentioned embodiments. For example, a crystalline choline salt that has an X-ray powder diffraction pattern comprising a peak at 7.5 degrees 2θ (±0.2 degrees 2θ) when measured using CuKα radiation and a $^{13}$C solid state NMR spectrum comprising peaks at chemical shifts of 175.1, 137.6 and 27.2 ppm (±0.2 ppm).

The present invention provides a process for the preparation of HEA which comprises crystallizing HEA under conditions described below. The precise conditions under which HEA is formed may be empirically determined and it is only possible to give methods which have been found to be suitable in practice.

It has been found that HEA may be prepared by a process comprising the following steps, which process is also an embodiment of the present invention:
(i) Combining Compound (1) with a suitable solvent and heating to about 60° C.;
(ii) Adding about 1.1 equivalents of choline hydroxide stock solution in a suitable solvent;
(iii) Cooling to about 5° C.;
(iv) Filtering the resulting slurry and rinsing the solid with a suitable solvent;
(v) Drying the solid at about 70° C. under vacuum.

Preferred solvents include acetonitrile and acetone. The most preferred solvent is acetonitrile. Suitable stock solutions of choline hydroxide include solutions in methanol or aqueous solutions, optionally diluted with acetonitrile. The preferred stock solution is a 45 wt % solution in methanol diluted with acetonitrile. The resulting crystals of HEA may be recovered by any conventional methods known in the art.

In the final steps (iv) and (v), the resulting solids obtained in step (iv) may be collected and dried at high temperature using conventional collection and high-temperature drying techniques, for example, filtration and vacuum oven.

In one preferred embodiment, Compound (1) is combined with acetonitrile at a ratio of 10 mL of acetonitrile per gram of Compound (1) in step (i) and the stock solution of choline hydroxide used in steps (ii) is prepared by diluting a 45% wt % solution of choline hydroxide in methanol with acetonitrile to 5 times the original volume.

In another embodiment, seeds of HEA obtained from a previous preparation are added during step (ii) after choline hydroxide is added.

In another embodiment, in step (iii), cooling takes place over about 4 hours while stirring. In another embodiment, the solid is dried for about 4 to 12 hours in step (v).

The process steps may of course be facilitated by conventional agitation techniques, e.g., stirring, and other conventional techniques as would be well understood for facilitating the process.

Crystalline MU

The Compound (1) has been isolated as a crystalline N-methyl-D-glucamine salt polymorph designated herein as "MU". In general, MU exhibits a characteristic X-ray powder diffraction ("XRPD") pattern with higher intensity peaks expressed in degrees 2θ (±0.2 degrees 2θ) at 2.5, 4.4, 5.1, 11.7, 15.5, 15.9 and 20.9.

Figure 5:
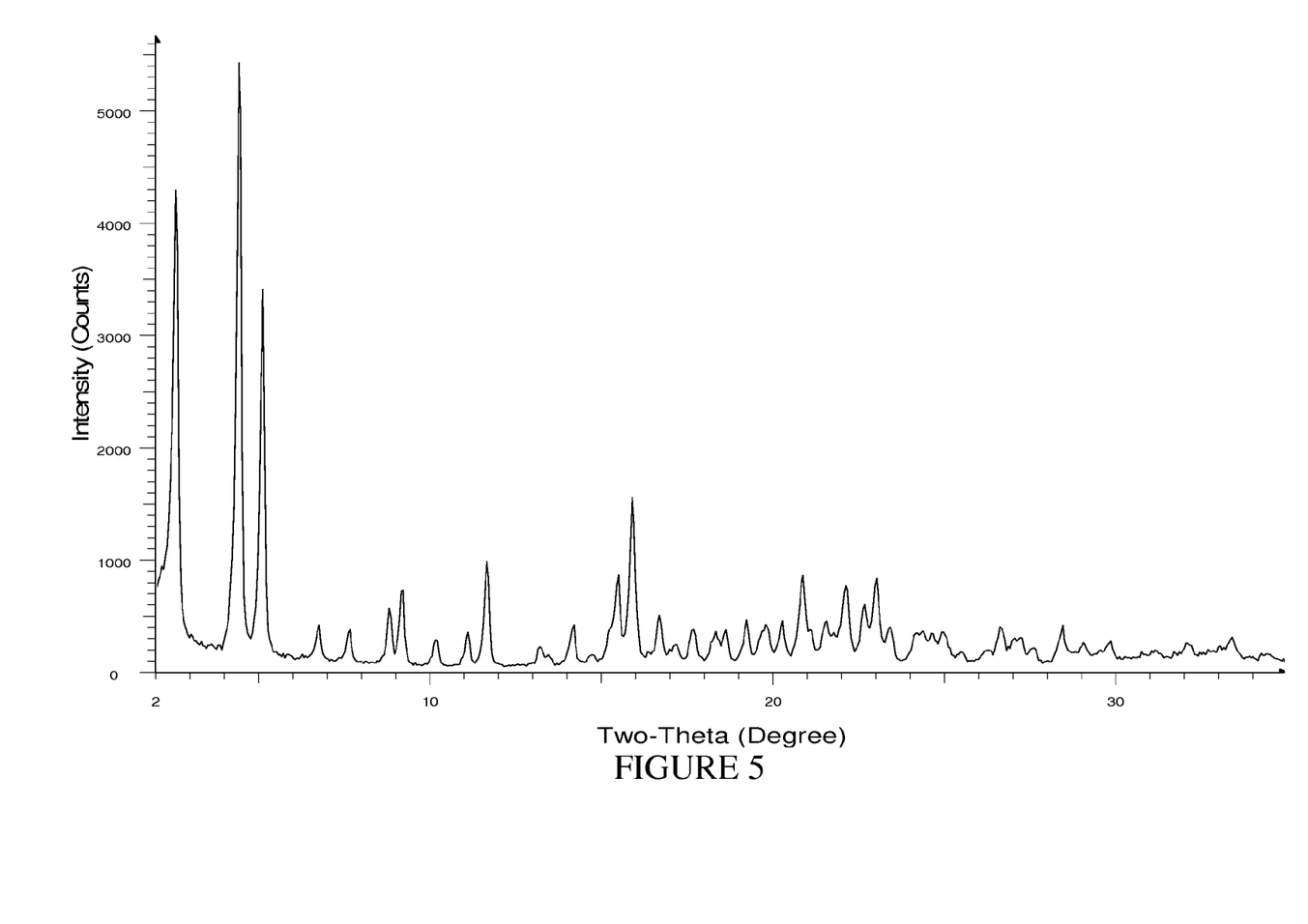
FIG. 5 is a characteristic X-ray Powder Diffraction pattern for crystalline MU.

The XRPD pattern of MU is shown in FIG. 5. The characteristic peak positions and relative intensities for the XRPD pattern in FIG. 5 is shown in Table 5 below (including both higher and lower intensity peaks).

TABLE 5

| Angle, 2θ, ° | Relative Intensity % |
|---|---|
| 2.5 | 79.3 |
| 4.4 | 100.0 |
| 5.1 | 62.8 |
| 8.8 | 10.4 |
| 9.2 | 13.3 |
| 11.7 | 18.3 |
| 15.5 | 15.9 |
| 15.9 | 28.6 |

TABLE 5-continued

| Angle, 2θ, ° | Relative Intensity % |
|---|---|
| 20.9 | 15.6 |
| 22.1 | 14.2 |
| 23.1 | 15.5 |

For MU crystals, Differential Scanning calorimetry (DSC) shows two broad endothermic events, one from 20° C. to 69° C. and the other from 155° C. to 187° C. Thermogravimetric Analysis (TGA) shows a weight loss of 3.13% associated with the first endothermic event (20° C. to 69° C.) that indicates MU is a hemipentahydrate form.

In one general embodiment, the present invention is directed to the crystalline N-methyl-D-glucamine salt of Compound (1), designated herein as "MU".

Another more specific embodiment is directed to crystalline MU that has at least the following characteristic: an X-ray powder diffraction pattern comprising a peak at 4.4 degrees 2θ (±0.2 degrees 2θ) when measured using CuKα radiation.

Another embodiment is directed to crystalline MU having an XRPD pattern comprising a peak at 4.4 degrees 2θ (±0.2 degrees 2θ) as described above and further comprising peaks at 2.5 and 5.1 degrees 2θ (±0.2 degrees 2θ) when measured using CuKα radiation.

Another embodiment is directed to crystalline MU having an XRPD pattern comprising a peak at 4.4 degrees 2θ (±0.2 degrees 2θ) as described above and further comprising peaks at 2.5, 5.1, 11.7 and 15.9 degrees 2θ (±0.2 degrees 2θ) when measured using CuKα radiation.

Another embodiment is directed to crystalline MU having an XRPD pattern comprising a peak at 4.4 degrees 2θ (±0.2 degrees 2θ) as described above and further comprising peaks at 2.5, 5.1, 11.7, 15.5, 15.9 and 20.9 degrees 2θ (±0.2 degrees 2θ) when measured using CuKα radiation.

Another embodiment is directed crystalline MU exhibiting an XRPD pattern substantially the same as that shown in FIG. 5.

MU exhibits a Solid-state NMR (ssNMR) pattern having $^{13}C$ chemical shifts (including both higher and lower intensity peaks) as reported in Table 6 below.

TABLE 6

| Chemical Shift (ppm) |
|---|
| 178.4 |
| 175.6 |
| 173.9 |
| 173.5 |
| 173.4 |
| 172.7 |
| 172.3 |
| 159.8 |
| 158.0 |
| 156.7 |
| 156.4 |
| 156.0 |
| 154.2 |
| 151.2 |
| 147.2 |
| 138.0 |
| 122.4 |
| 118.8 |
| 116.4 |
| 114.0 |
| 111.6 |
| 95.7 |
| 79.4 |
| 78.9 |

TABLE 6-continued

| Chemical Shift (ppm) |
|---|
| 74.7 |
| 70.6 |
| 70.4 |
| 67.7 |
| 67.2 |
| 59.7 |
| 59.2 |
| 58.6 |
| 58.2 |
| 53.5 |
| 51.7 |
| 42.1 |
| 41.7 |
| 41.6 |
| 38.6 |
| 37.5 |
| 35.1 |
| 34.7 |
| 34.4 |
| 34.2 |
| 33.8 |
| 27.0 |
| 24.7 |
| 23.9 |
| 20.8 |
| 19.2 |
| 18.9 |

All chemical shifts reported and claimed herein are accurate to within ±0.2 ppm unless otherwise indicated.

Figure 6:
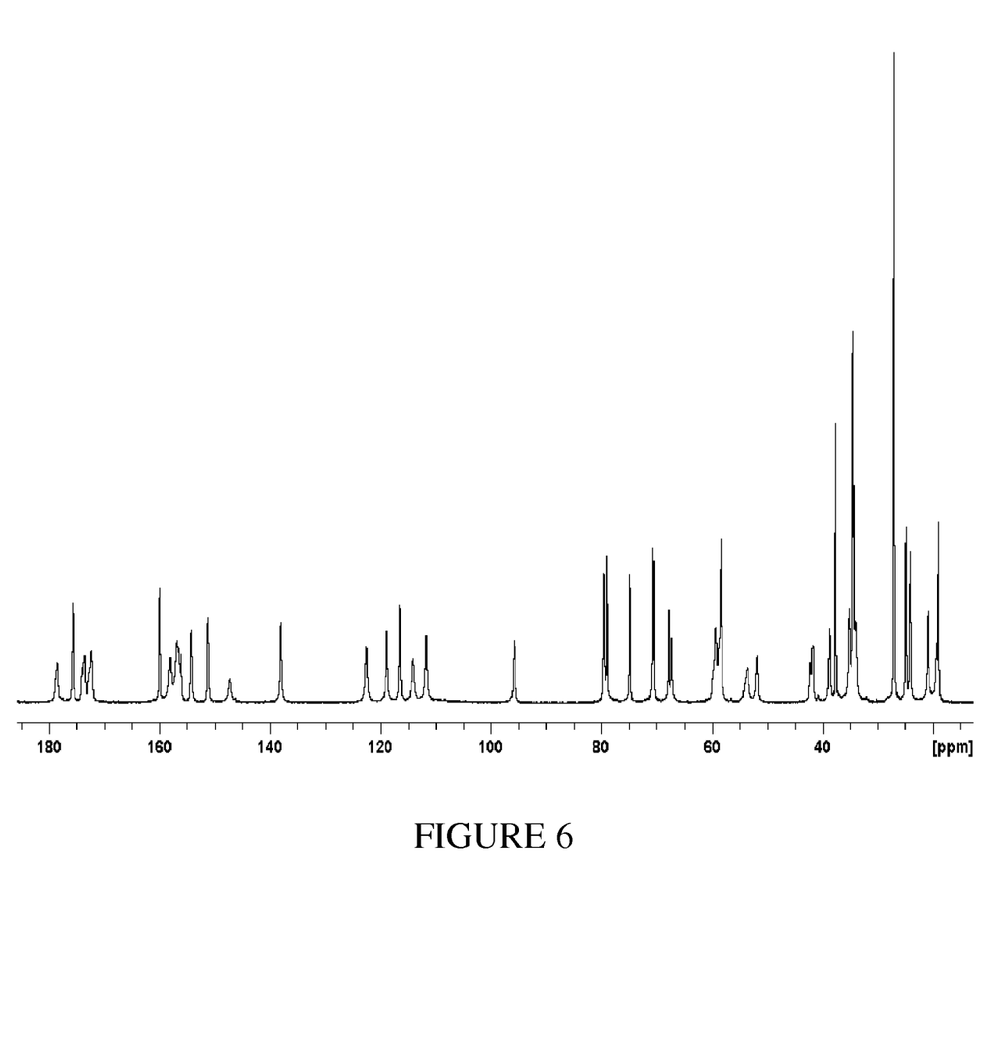
FIG. 6 is a characteristic $^{13}$C Solid State NMR spectrum for crystalline MU.

A representative $^{13}C$ ssNMR spectrum of MU is shown in FIG. 6.

One general embodiment is directed to a crystalline N-methyl-D-glucamine salt of Compound (1) that has a $^{13}C$ solid state NMR spectrum comprising peaks at chemical shifts of 178.4, 138.0 and 27.0 ppm (±0.2 ppm). These chemical shift peaks are believed sufficient to characterize the MU salt of Compound (1) and distinguish it from other crystalline forms.

Another embodiment is directed to a crystalline N-methyl-D-glucamine salt of Compound (1) that has a $^{13}C$ solid state NMR spectrum comprising peaks at chemical shifts of 178.4, 175.6, 159.8, 154.2, 151.2, 138.0 and 27.0 ppm (all ±0.2 ppm).

Another embodiment is directed to a crystalline N-methyl-D-glucamine salt of Compound (1) that has a $^{13}C$ solid state NMR spectrum comprising peaks at chemical shifts of 178.4, 175.6, 173.4, 172.3, 159.8, 154.2, 151.2, 138.0, 27.0, 24.7 and 20.8 ppm (all ±0.2 ppm).

Another embodiment is directed to the crystalline N-methyl-D-glucamine salt of Compound (1) exhibiting an $^{13}C$ ssNMR spectrum substantially the same as that shown in FIG. 6.

Another embodiment is directed to a crystalline N-methyl-D-glucamine salt of Compound (1) having both an XRPD pattern and $^{13}C$ ssNMR spectrum according to any combination of the above-mentioned embodiments. For example, a crystalline N-methyl-D-glucamine salt that has an X-ray powder diffraction pattern comprising a peak at 4.4 degrees 2θ (±0.2 degrees 2θ) when measured using CuKα radiation and a $^{13}C$ solid state NMR spectrum comprising peaks at chemical shifts of 178.4, 138.0 and 27.0 ppm (±0.2 ppm).

The present invention provides a process for the preparation of MU which comprises crystallizing MU under conditions described below. The precise conditions under which MU is formed may be empirically determined and it is only possible to give methods which have been found to be suitable in practice.

It has been found that MU may be prepared by a process comprising the following steps, which process is also an embodiment of the present invention:

(i) Combining Compound (1) with 1 equivalent of N-Methyl-D-Glucamine in a suitable solvent;
(ii) Heating the mixture to about 50° C.;
(iii) Charge a suitable solvent to reduce the solubility of MU over 4 hrs;
(iv) Cool the slurry to about 20° C. over 3 hrs;
(v) Filter the slurry and rinse the resulting solid with a suitable solvent or solvent mixture;
(vi) Dry the solid at about ≦30° C. under vacuum.

Suitable solvents include methyl acetate (MeOAc)/$H_2O$ or isopropyl alcohol (IPA)/$H_2O$. The preferred solvent is MeOAc/$H_2O$ mixture. The resulting crystals of MU may be recovered by any conventional methods known in the art.

In one preferred embodiment, Compound (1) and 1 equivalent of N-Methyl-D-Glucamine are combined in MeOAc/$H_2O$ (9.2 wt %) at a ratio of 4.68 g of MeOAc/$H_2O$ per gram of Compound (1) in step (i), are heated to about 50° C. and 7.13 g of MeOAc per gram of Compound (1) is added over for 4 hours in step (iii) and rinsed with MeOAc/$H_2O$ mixture (1.75 g of MeOAc+0.035 g $H_2O$ per gram of Compound (1)) in step (v).

In another embodiment, seeds of MU, obtained from a previous preparation are added during step (iii).

The process steps may of course be facilitated by conventional agitation techniques, e.g., stirring, and other conventional techniques as would be well understood for facilitating the process.

Salt Characteristics

The tromethamine salt form TH and the choline salt HEA have been unexpectedly found to have unique properties making them particularly advantageous in pharmaceutical formulation processing. In particular, TH and HEA have certain properties that would provide for easier characterization, processing and handling during manufacturing.

First, TH was unexpectedly found to exist in a non-solvated and non-hygroscopic or slightly hygroscopic (at ambient temperature up to 85% RH) crystalline form. HEA was also found to exist in a non-solvated and non-hygroscopic crystalline form (at ambient temperature up to 85% RH). These are not predictable properties. For example, the sodium salt (NA) was found to exist as a variable hydrate which may create challenges in consistent formulation characterization, manufacturing (e.g. difficulty drying) and handling.

Furthermore TH was unexpectedly found to have over a 10 fold greater dissolution rate at pH 6.8 than the sodium salt or HEA as shown in Table 7. HEA was comparable to the sodium salt. Enhanced dissolution may be advantageous for absorption and bioavailability.

TABLE 7

| Compound | Dissolution Rate (μg/min/mL) |
|---|---|
| TH | 64.4 |
| HEA | 1.1 |
| NA | 1.3 |

The methods used in generating these results are described below in the Methods of Characterization section.

The above results obtained with the various crystalline salts of Compound (1) are unexpected because it is generally not possible to predict such differences in hygroscopic properties, solvate form or solubility between different salt forms of a compound, and in particular for Compound (1), even after such forms have been successfully prepared.

Pharmaceutical Compositions and Methods

The aforementioned forms of Compound (1), including the TH, HEA and MU salt forms, are useful as anti-HCV agents in view of the demonstrated inhibitory activity of Compound (1) against HCV NS3 serine protease. These forms are therefore useful in treatment of HCV infection in a mammal and can be used for the preparation of a pharmaceutical composition for treating an HCV infection or alleviating one or more symptoms thereof in a patient. The appropriate dosage amounts and regimens for a particular patient can be determined by methods known in the art and by reference to the disclosure in U.S. Pat. Nos. 6,323,180 and 7,585,845. Generally, a therapeutically effective amount for the treatment of HCV infection in the mammal is administered. In one embodiment, about 50 mg to 1000 mg, more preferably from about 120 mg to about 480 mg, is administered per adult human per day in single or multiple doses.

Specific optimal dosage and treatment regimens for any particular patient will of course depend upon a variety of factors, including the age, body weight, general health status, sex, diet, time of administration, rate of excretion, drug combination, the severity and course of the infection, the patient's disposition to the infection and the judgment of the treating physician. In general, the compound is most desirably administered at a concentration level that will generally afford anti-virally effective results without causing any harmful or deleterious side effects.

The TH, HEA and MU crystalline salt forms of Compound (1) at a selected dosage level is typically administered to the patient via a pharmaceutical composition. See, e.g., the descriptions in U.S. Pat. Nos. 6,323,180 and 7,585,845 for the various types of compositions that may be employed in the present invention. The pharmaceutical composition may be administered orally, parenterally or via an implanted reservoir. The term parenteral as used herein includes subcutaneous, intracutaneous, intravenous, intramuscular, intra-articular, intrasynovial, intrasternal, intrathecal, and intralesional injection or infusion techniques. Oral administration or administration by injection are preferred.

The pharmaceutical compositions of this invention may contain any conventional non-toxic pharmaceutically-acceptable carriers, diluents, adjuvants, excipients or vehicles. In some cases, the pH of the formulation may be adjusted with pharmaceutically acceptable acids, bases or buffers to enhance the stability of the formulated compound or its delivery form.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example. Tween 80) and suspending agents.

The pharmaceutical compositions may also be in the form of an oral pharmaceutical composition comprising the TH, HEA or MU salt of Compound (1), or mixtures thereof, and at least one pharmaceutically acceptable carrier or diluent. The oral pharmaceutical compositions may be orally administered in any orally acceptable dosage form including, but not limited to, tablets, capsules (e.g., hard or soft gelatin capsules), including liquid-filled capsules, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. Examples of soft gelatin capsules that can be used include those disclosed in EP 649651 B1 and U.S. Pat. No. 5,985,321. When aqueous suspensions are administered orally, the active ingredient is combined with emulsifying and suspending agents. If desired, certain sweetening and/or flavoring and/or coloring agents may be added.

Other suitable vehicles or carriers for the above noted formulations and compositions can be found in standard pharmaceutical texts, e.g. in "Remington's Pharmaceutical Sciences", 19$^{th}$ ed., Mack Publishing Company, Easton, Pa., 1995.

Certainly, when the crystalline TH, HEA or MU salt is formulated in a liquid vehicle, for example, as a liquid solution or suspension for oral administration or by injection, including for example in liquid-filled capsules, the salt loses its crystalline nature. Nevertheless, the final liquid-based pharmaceutical composition contains the novel TH, HEA or MU salt of Compound (1) and it is therefore to be considered a separate to embodiment embraced by the present invention.

Methods of Characterization

1. X-Ray Powder Diffraction

X-ray powder diffraction analyses were conducted on a Bruker AXS X-Ray Powder Diffractometer Model D8 Discover, available from Bruker AXS, Inc. of Madison, Wis., using CuKa radiation. Step scans were run from 2 to 35° 2-theta, at 0.05° per step, 4 sec per step. A reference quartz standard was used to check instrument alignment. Samples were prepared for analysis by filing a zero background silicon holder.

2. DSC Analysis

TA instruments Q1000 was used for DSC analysis. Approximately 5 mg of sample was weighed into a hermetic aluminum pan, open. Standard ramp mode was used from 20° C. to 300° C. with 10° C./min heating rate. The DSC cell was purged with 50 mL/min nitrogen while running.

3. TGA Analysis

TA instruments Q500 was used for TGA analysis. Approximately 10 mg of sample was placed on a tared platinum TGA pan. Sample was scanned from 25° C. to 300° C. with 10° C./min heating rate. TGA furnace was purged with 60 mL/min nitrogen while the balance was purged with 40 mL/min nitrogen.

4. Dynamic Vapor Sorption

Dynamic water sorption analyses were performed using Surface Measurement Systems DVS or DVS-HT, or VTI SGA-100 instruments. Sample sizes ranged from 4 mg to 13 mg. Three cycles of water sorption/desorption were run at 25° C. with change of relative humidity from 5-10% increments from 5% to 95%. The criteria for the step were weight change less than or equal to 0.002% or maximum time of 3 hours.

5. Solid State NMR

Solid-state NMR (SSNMR) data was acquired on a Bruker Avance III NMR spectrometer (Bruker Biospin, Inc., Billerica, Mass.) at 9.4 T ($^1$H=400.46 MHz, $^{13}$C=100.70 MHz). Samples were packed in 4 mm O.D. zirconia rotors with Kel-F® drive tips. A Bruker model 4BL CP BB WVT probe was used for data acquisition and sample spinning about the magic-angle (54.74°). Sample spectrum acquisition used a spinning rate of 12 kHz. A standard cross-polarization pulse sequence was used with a ramped Hartman-Hahn match pulse on the proton channel at ambient temperature and pressure. The pulse sequence used a 5 millisecond contact pulse and a 2 second recycle delay. Two-pulse phase modulated (tppm) decoupling was also employed in the pulse sequence. No exponential line broadening was used prior to Fourier transformation of the free incution decay. Chemical shifts were referenced using the secondary standard of adamantane, with the upfield resonance being set to 29.5 ppm. The magic-angle was set using the $^{79}$Br signal from KBr powder at a spinning rate of 5 kHz.

6. Dissolution Studies

Intrinsic dissolution rates were evaluated using Van Kel VK7000 dissolution tester and 400 mL dissolution bath with a rotation rate of 100 rpm at 37° C. Samples were prepared using approximately 50 mg of API in a 6 mm diameter Wood's die with compression force of 3 kN and 15 seconds dwell time by Carver press. The test was performed in 400 mL of pH 6.8 (20 mM sodium phosphate). Samples were collected at 2, 5, 10, 15, 20, 25, and 30 minutes, and the collected samples were unfiltered or filtered using 0.2 nm PDVF filter. The concentrations of the drug were determined by HPLC using isocratic Method with fluorescence detection.

In order that this invention be more fully understood, the following examples are set forth. These examples are for the purpose of illustrating embodiments of this invention, and are not to be construed as limiting the scope of the invention in any way. The starting material used in the examples, Compound (1), may be prepared by methods disclosed in U.S. Pat. Nos. 6,323,180, 7,514,557 and 7,585,845.

EXAMPLES

Example 1

Preparation of the Tromethamine Salt of Compound (1)

Compound (1) (5 g) and tris(hydroxymethyl)aminomethane (0.696 g) are combined in 50 mL of acetone. The mixture is stirred and heated to 50° C. and stirred at that temperature for 4 hours. The resulting slurry is cooled slowly to 20° C. while stirring. The cooled mixture is stirred a total of 12 hours. The resulting mixture is vacuum filtered and the resulting solid is rinsed with acetone (2×10 mL). The solid is dried at 70° C. under vacuum for 12 hours to provide the Tromethamine salt of Compound (1) (TH).

The XRPD pattern of TH is shown in FIG. 1 and the $^{13}$C ssNMR spectrum of TH is shown in FIG. 2.

Example 2

Preparation of the Choline Salt of Compound (1)

Compound (1) (5 g) is combined and stirred with 50 mL of acetonitrile and heated to 60° C. 4.52 mL of a choline hydroxide stock solution, previously prepared by diluting 5 mL of choline hydroxide 45 wt % solution in MeOH with acetonitrile to a total volume of 25 mL, is slowly added over a period of 6 hours while stirring at 60° C. The mixture is stirred and cooled slowly to 5° C. over a period of 4 hours. The slurry is then filtered and the resulting solid is washed with acetonitrile (2×10 mL). The solid is then dried at 70° C. under vacuum for 12 hours to provide the choline salt of Compound (1) (HEA).

The XRPD pattern of HEA is shown in FIG. 3 and the $^{13}$C ssNMR spectrum of HEA is shown in FIG. 4.

Example 3

Preparation of the N-Methyl-D-Glucamine Salt of Compound (1)

Compound (1) (20 g) and N-Methyl-D-Glucamine (4.49 g) are combined with 8.63 g H$_2$O and 85 g Methyl Acetate (MeOAc). The mixture is stirred and heated to 50° C. 142.5 g MeOAc is charged into the mixture over ≧4 hours (seeding is preferred but not required before the MeOAc addition). The resulting slurry is cooled to 20° C. over ≧3 hours while stirring. The resulting mixture is filtered and the resulting solid is rinsed with a MeOAc/H$_2$O mixture (35.15 g MeOAc+ 0.717 g H$_2$O). The solid is dried at ≦30° C. under vacuum for ≧12 hours to provide the N-Methyl-D-Glucamine salt of Compound (1) (MU).

The XRPD pattern of MU is shown in FIG. 5 and the $^{13}$C ssNMR spectrum of MU is shown in FIG. 6.

The invention claimed is:

1. A crystalline tromethamine salt of the compound of the following formula (I):

having an X-ray powder diffraction pattern comprising a peak at 5.9 degrees 2θ (+0.2 degrees 2θ) when measured using CuKα radiation and/or having a $^{13}$C solid state NMR spectrum comprising peaks at chemical shifts of 178.3, 138.1 and 27.1 ppm (+0.2 ppm).

2. The crystalline salt according to claim 1, having an X-ray powder diffraction pattern comprising a peak at 5.9 degrees 2θ (±0.2 degrees 2θ) when measured using CuKα radiation.

3. The crystalline salt according to claim 1, having an X-ray powder diffraction pattern comprising peaks at 5.9, 10.0 and 20.9 degrees 2θ (±0.2 degrees 2θ) when measured using CuKα radiation.

4. The crystalline salt according to claim 1, having an X-ray powder diffraction pattern comprising peaks at 5.9, 10.0, 16.7, 20.3 and 20.9 degrees 2θ (±0.2 degrees 2θ) when measured using CuKα radiation.

5. The crystalline salt according to claim 1, having an X-ray powder diffraction pattern comprising peaks at 5.9, 9.8, 10.0, 16.4, 16.7, 20.3, 20.9 and 22.6 degrees 2θ (±0.2 degrees 2θ) when measured using CuKα radiation.

6. The crystalline salt according to claim 1, that has a $^{13}$C solid state NMR spectrum comprising peaks at chemical shifts of 178.3, 138.1 and 27.1 ppm (±0.2 ppm).

7. The crystalline salt according to claim 1, that has a $^{13}$C solid state NMR spectrum comprising peaks at chemical shifts of 178.3, 173.9, 173.1, 150.2, 147.9, 138.1 and 27.1 ppm (all ±0.2 ppm).

8. The crystalline salt according to claim 1, that has a $^{13}$C solid state NMR spectrum comprising peaks at chemical shifts of 178.3, 176.0, 173.9, 173.1, 150.2, 147.9, 138.1, 36.7, 27.1, 22.8 and 18.6 ppm (all ±0.2 ppm).

9. The crystalline salt according to claim 1, that has an X-ray powder diffraction pattern comprising a peak at 5.9 degrees 2θ (±0.2 degrees 2θ) when measured using CuKα radiation and a $^{13}$C solid state NMR spectrum comprising peaks at chemical shifts of 178.3, 138.1 and 27.1 ppm (±0.2 ppm).

10. A pharmaceutical composition comprising a salt according to claim 1, and at least one pharmaceutically acceptable carrier or diluent.

* * * * *